(12) United States Patent
Taylor et al.

(10) Patent No.: US 6,652,722 B2
(45) Date of Patent: Nov. 25, 2003

(54) SENSOR FOR MEASURING THE PARTIAL PRESSURE OF A GAS OF THE TYPE COMPRISING AN ELECTROCHEMICAL CELL AND A GASEOUS DIFFUSION BARRIER

(75) Inventors: Malcolm Taylor, Beaurains (FR); Lionel Félix Witrant, Villeneuve d'Ascq (FR); Jean-Marie Beaumont, Goeulzin (FR); Daniel Lucien Gaston Chevalier, Beaurains (FR)

(73) Assignee: Oldham, Arras Cedex (FR)

( * ) Notice: Subject to any disclaimer, the term of this patent is extended or adjusted under 35 U.S.C. 154(b) by 96 days.

(21) Appl. No.: 09/897,883

(22) Filed: Jul. 5, 2001

(65) Prior Publication Data
US 2002/0063057 A1 May 30, 2002

(30) Foreign Application Priority Data
Jul. 4, 2000 (FR) .............................. 00 08695

(51) Int. Cl.[7] .......................................... G01N 27/404
(52) U.S. Cl. ............................... 204/415; 205/783
(58) Field of Search ................... 204/415, 432, 204/431

(56) References Cited

U.S. PATENT DOCUMENTS

| 4,182,666 A | * | 1/1980 | Dickinson et al. |
| 4,495,051 A | | 1/1985 | Fujita et al. |
| 4,689,135 A | | 8/1987 | Lungu et al. |
| 5,879,527 A | * | 3/1999 | Kiesele et al. |

FOREIGN PATENT DOCUMENTS

WO    WO 99/24826    5/1999

* cited by examiner

*Primary Examiner*—T. Tung
(74) *Attorney, Agent, or Firm*—Young & Thompson

(57) ABSTRACT

Sensor for measuring the partial pressure of a gas in a gaseous medium, includes an electrochemical cell and a diffusion barrier with a porous membrane situated above an orifice made in a component surmounting a casing enclosing said electrochemical cell.

19 Claims, 1 Drawing Sheet

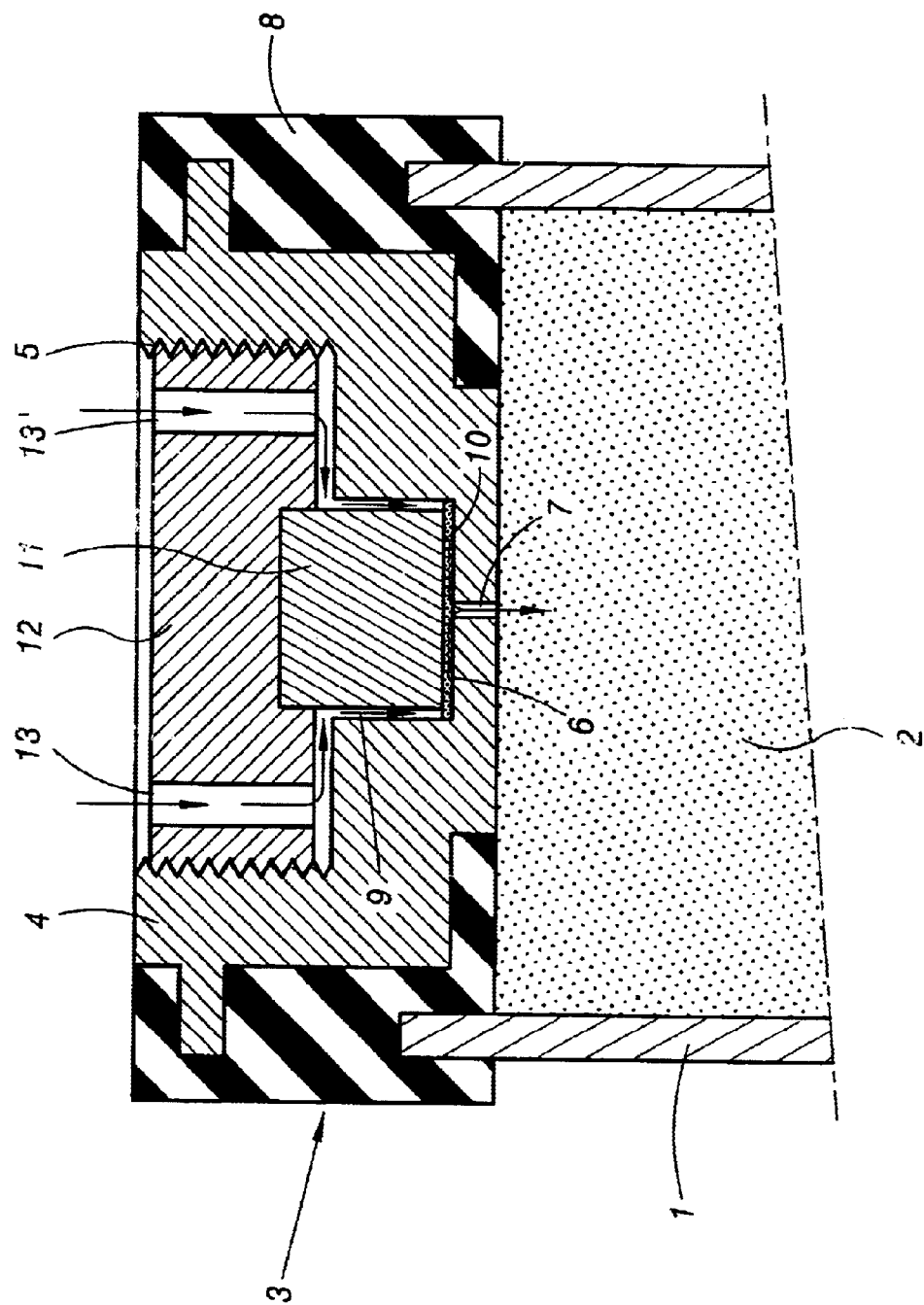

SENSOR FOR MEASURING THE PARTIAL PRESSURE OF A GAS OF THE TYPE COMPRISING AN ELECTROCHEMICAL CELL AND A GASEOUS DIFFUSION BARRIER

BACKGROUND OF THE INVENTION

The invention relates to the measurement of the partial pressure of a given gas in a gaseous medium, for example the measurement of the partial pressure of oxygen in the air.

More precisely, it relates to sensors for measuring this partial pressure using an electrochemical cell. This cell consists of a cathode made of a noble metal (such as platinum), an anode made of lead, and an electrolyte, (such as soda).

DESCRIPTION OF THE RELATED ART

It is conventional practice to make the anode in porous form (from lead wool for example) and to impregnate it with electrolyte. The cathode and the anode are boxed in a casing while being separated by an insulating membrane permeable to the electrolyte. Means of feeding and of extracting the gas to be analyzed are associated with this cell. These sensors also comprise a diffusion barrier which limits the gaseous flux entering the cell, in such a way as to endow the sensor with better sensitivity. It is preferable, in general, for the cell to detect the partial pressure of oxygen in the air to be analyzed and not its concentration (since the partial pressure of oxygen is more representative of any risks incurred by persons breathing this atmosphere, in particular in partially evacuated premises) Certain sensors use nonporous membranes as diffusion barrier, as described for example in the document U.S. Pat. No. 4,495,051. For this purpose it is necessary to use membranes of very small thickness. Above all, these membranes are very sensitive to temperature variations, thereby limiting the accuracy and the reliability of the sensors thus constructed.

In another type of known sensor the diffusion barrier achieves a Knudsen-type mode of diffusion. This mode of diffusion is obtained by using as the main element of the diffusion barrier a membrane made of a porous material having sufficiently small pores for the number of collisions between the gas molecules and the walls of the pores to be much larger than the number of intermolecular collisions. As a first approximation, it may be stated that the diameter of the pores must be much smaller than the mean free path of the molecules, which is of the order of $9.5\ 10^{-8}$ m at ambient pressure and temperature.

The membrane must, furthermore, possess low thermal expansion between $-10$ and $40°$ C. (the customary temperatures of use of these cells), high mechanical stability over several years, and insensitivity to the humidity factor of the medium analyzed.

Such membranes may, in a known manner, be made from specially prepared PTFE strips, such as described for example in the document GB-A-2,049,952 which relates to sensors for measuring the partial pressure of oxygen of the above type. The various elements of the electrochemical cell are contained in a casing, plugged at its upper end by a metal cover. This metal cover comprises a central perforation of small diameter (of the order for example of 0.12 mm). In a preferred embodiment, the diffusion barrier consists of a strip of PTFE, placed above this perforation and gripped between two strips of adhesive tape which increase the diffusion path of the atmosphere to be analyzed. The whole is compressed by a metal lid sealed over the cover (for example by welding), drilled with small holes permitting access of the gas to the periphery of the diffusion barrier. Appropriate sensitivity of the sensor is thus obtained by limiting the flux of oxygen which travels through it and by compelling it to cross the largest possible part of the PTFE strip constituting the diffusion barrier.

This construction of the sensor has the following drawback however. The metal lid must be force fitted, by hammering, in such a way as to compress the PTFE strip so as to make it fill the entire space crossed by the gas to be analyzed. The hammering results in localized application of considerable loads which may lead to impairment of the strip and to enhanced degradation of its mechanical properties over time. Under these conditions, the pores of the diffusion barrier are damaged and the sensor rapidly becomes unreliable.

SUMMARY OF THE INVENTION

The aim of the invention is to propose a configuration of the upper part of a sensor for measuring the partial pressure of a gas of the above-described type endowing the sensor with enhanced reliability and enhanced durability.

Accordingly, the subject of the invention is a sensor for measuring the partial pressure of a gas in a gaseous medium, of the type comprising an electrochemical cell and a porous diffusion barrier situated upstream of said cell along the course of said gaseous medium, said diffusion barrier comprising a porous membrane having very fine pores, situated above an orifice made in a component surmounting a casing enclosing said electrochemical cell, characterized in that it comprises:

a cap surmounting said casing in a leaktight manner, said cap including or consisting of a first component provided with a central recess in the bottom of which said orifice is made, a housing being provided in the bottom of said recess around said orifice so as to place said porous membrane therein;

a second component applying said membrane against the bottom of said housing with a clearance between said second component and the lateral wall of the housing permitting the passage of the gaseous medium to be analyzed toward said membrane; and a third component held in said central recess of said first component in such a way as to exert on said second component the pressure required for the application of said membrane against the bottom of said recess, and comprising at least one orifice permitting the passage of said gaseous medium from outside the sensor up to said membrane.

Said first, second and third components are preferably made of a corrosion-insensitive metallic material exhibiting low expansion between $-10$ and $40°$ C., such as SUS 316L stainless steel.

In one embodiment, said cap comprises a polymer envelope laterally jacketing said first metal component, and said envelope ensures leaktight contact between the cap and the casing enclosing the electrochemical cell.

Preferably, the central recess of said first component comprises a thread on its lateral wall, and the third component comprises on its external wall a thread corresponding to the previous one, so as to ensure the securing together of the first and third components and the holding of the third component in a position where it can ensure the application of the second component against the porous membrane.

As will have been understood, the invention consists firstly in effecting the plugging of the upstream part of the casing enclosing the electrochemical cell (that is to say of the part via which the gas to be analyzed enters the sensor) by a cap comprising a first recessed component. The bottom of this recess comprises a housing in the bottom of which is made the orifice via which the gas to be analyzed enters the electrochemical cell. A patch made of a porous material able to constitute a Knudsen-type diffusion barrier is arranged in the bottom of this housing. The recess is filled in at its upper part with another perforated component which exerts a pressure on an intermediate component; the latter is itself placed in the housing enclosing the porous patch with a very slight clearance permitting the passage of the gas to be analyzed.

The pressure exerted on the intermediate component is transmitted by the latter to the porous patch, so that the latter preferably occupies the entire bottom of its housing. Thus, the gas to be analyzed crosses the porous patch following the longest possible path, thereby optimizing the performance of the sensor in terms of sensitivity. Moreover, the compressive loads applied to the porous patch are also distributed over the whole of its surface, both during the mounting of the sensor and during its use. Hence, no zones which, at one time or another, would be subjected to an excessive load which might impair the patch are created on the latter.

BRIEF DESCRIPTION OF THE DRAWING

The invention will be better understood on reading the description which follows, given with reference to the single appended FIGURE which shows, viewed in longitudinal section, the upper part of an exemplary sensor for measuring the partial pressure of a gas according to the invention.

DESCRIPTION OF THE PREFERRED EMBODIMENT

The sensor for measuring the partial pressure of a gas in a gaseous medium according to the invention, as represented in the single FIGURE, comprises, in a known manner, a casing 1 of, for example, cylindrical general shape. It encloses the electrochemical cell 2 which comprises an anode, a cathode and an electrolyte. This electrochemical cell 2 can be of any type known per se, and it will therefore not be described and represented in detail.

According to the invention, the casing 1 is plugged at its upper part by a cap 3. This cap is composed firstly of a first metal component 4, provided with a central recess 5, in the bottom 6 of which is made an orifice 7 of small dimensions (for example 0.3 mm in diameter and 0.75 mm in depth), opening out onto the upper part of the electrolytic cell 2. This first metal component 4 is jacketed laterally by a polymer envelope 8. It is this envelope 8 which ensures the leaktight joint between the cap 3 and the upper part of the casing 1. This leaktightness is obtained, for example, by means of ultrasonic welding of the envelope 8 to the casing 1.

A housing 9 is provided in the bottom 6 of the recess 5, and it is substantially at the center of the bottom of this housing 9 that the orifice 7 is made. At the bottom of this housing 9 is placed a patch 10 of a material able to constitute a Knudsen-type diffusion barrier for the gas whose partial pressure in the gaseous medium in which the sensor is immersed is to be measured, for example for oxygen.

This housing 9 is also able to receive a second metal component 11, whose outside diameter is only very slightly smaller than the diameter of the housing 9, so as to leave a minimal clearance (of 0.05 mm for example) between this second component and the lateral wall of the housing 9, so permitting the passage of the gaseous medium to be analyzed.

The cap 3 also comprises a third metal component 12, intended to be inserted inside the recess 5, and to exert a pressure on the second metal component 11. This pressure is transmitted to the porous membrane 10, in such a way as to ensure, preferably, the complete filling of the bottom of the housing 9 by said membrane. In the example represented in the single FIGURE, the lateral wall of the recess 5 comprises a thread, and on its lateral wall the third metal component 12 comprises a corresponding thread, allowing the screwing of the third metal component 12 inside the recess 5. This screwing is effected during the mounting of the sensor, in such a way as to achieve a locking of the third metal component 12 inside the recess 5 when the porous membrane 10 is suitably compressed. At least one orifice 13, 13' is drilled vertically through the third metal component 12, in such a way as to feed the gaseous medium extracted from the medium to be analyzed into the narrow space separating the housing 9 and the second metal component 11. The gaseous medium to be analyzed is thus able to reach the porous membrane 10, to cross it and then to enter the orifice 7 and finally the electrochemical cell 2 so as to be analyzed therein in the known manner.

It is vital for the second 11 and third 12 metal components to be separate from one another. Specifically, when mounting the sensor, the porous membrane 10 must not undergo a shearing load applied to its upper surface, which would be the case if the metal component in contact with it underwent a rotation during the screwing operation. For this same reason, it is vital for the contact between the second 11 and third 12 metal components to occur with very reduced friction, since otherwise the rotational motion of the third metal component 12 during its screwing could be at least partially transmitted to the second metal component 11, which would lead to the impairment of the porous membrane 10 or to its deformation. In practice, the second 11 and third 12 metal components are made with contact surfaces exhibiting a roughness Ra of better than 0.8.

The various metal components 4, 11, 12 just mentioned need to be made from a corrosion-insensitive material, since these sensors need to be usable in polluted or humid environments. A SUS 316L-type stainless steel is a material particularly indicated for making these various components, since apart from its insensitivity to corrosion, it exhibits the small thermal expansion characteristics demanded between −10 and 40° C.

As a variant, it would be possible to make all or some of the various metal components 4, 11, 12 just described from a plastic material, provided that the latter makes it possible to achieve sufficient machining accuracy, in particular in respect of the threads mentioned earlier, and the low friction required between the second and third components 11, 12.

Conversely, the polymer envelope 8 of the first metal component 4 could be dispensed with, and the latter could be screwed or welded directly onto the upper part of the casing 1, provided that sufficient leaktightness is obtained at the level of this bond.

As a variant, the third component 12 can be held in place in such a way as to exert a pressure on the second component 11 not by virtue of a thread, but by virtue of another type of device, for example by means of a clip.

It will have been noted that the sensor according to the invention does not require the presence of adhesive tape which would be added to the porous membrane 10 and which the gas to be analyzed would be compelled to cross before reaching the electrochemical cell 2.

Preferably, the upper part of the cap 3 is surmounted by a cover made of a porous material (not represented in the single FIGURE), in such a way as to prevent water or dust from penetrating the entry orifices 13, 13' for the gas to be analyzed.

The invention finds a favored application in the field of the analysis of ambient air by measuring the partial pressure of oxygen. It goes without saying that it could be used on sensors operating according to the same principle and allowing the analysis of types of atmosphere other than air, by measuring the partial pressure of a specified gas.

What is claimed is:

1. Sensor for measuring the partial pressure of a gas in a gaseous medium, comprising an electrochemical cell (2) and a porous diffusion barrier situated upstream of said cell along the course of said gaseous medium, said diffusion barrier comprising a porous membrane (10) having very fine pores, situated above an orifice (7) made in a component surmounting a casing (1) enclosing said electrochemical cell (2), characterized in that it comprises:

a cap (3) surmounting said casing (1) in a leaktight manner, said cap (3) including a first component (4) provided with a central recess (5) in the bottom of which said orifice (7) is made, a housing (9) being provided in the bottom (6) of said recess around said orifice (7) so as to place said porous membrane (10) therein;

a second component (11) applying said membrane (10) against the bottom (6) of said housing (9) with a clearance between said second component (11) and the lateral wall of the housing (9) permitting the passage of the gaseous medium to be analyzed toward said membrane (10); and a third component (12) held in said central recess (5) of said first component (4) in such a way as to exert on said second component (11) the pressure required for the application of said membrane (10) against the bottom (6) of said recess (9), and comprising at least one orifice (13, 13') permitting the passage of said gaseous medium from outside the sensor up to said membrane (10).

2. Sensor according to claim 1, characterized in that said first (4), second (11) and third (12) components are made of a corrosion-insensitive metallic material exhibiting low expansion between −10 and 40° C.

3. Server of claim 2, wherein said metallic material is SUS 316L stainless steel.

4. Sensor according to claim 1, characterized in that said cap (3) comprises a polymer envelope laterally jacketing said first metal component, and in that said envelope (8) ensures leaktight contact between the cap (3) and the casing (1) enclosing the electrochemical cell (2).

5. Sensor according to claim 1, characterized in that the central recess (5) of the first component comprises a thread on its lateral wall, and in that the third component (12) comprises on its external wall a thread corresponding to the previous one, so as to ensure the securing together of the first (4) and third (12) components and the holding of the third component (12) in a position where it can ensure the application of the second component (11) against the porous membrane (10).

6. A sensor for measuring the partial pressure of a gas in a gaseous medium, comprising:

a cylindrical casing;

an electrochemical cell enclosed within the casing, the electrochemical cell comprising an anode, a cathode, and an electrolyte;

a cap plugging an upper part of the casing, the cap comprising an outer polymer envelope leaktightly joined to the upper part of the casing, a first metal component jacketed laterally by the polymer envelope, the first metal component having a central recess and an orifice in a bottom of the recess, the orifice opening out onto an upper part of the electrochemical cell;

a housing substantially centered in the bottom of the recess;

a porous membrane located at a bottom of the housing and over the orifice, the membrane forming a diffusion barrier for the gas whose partial pressure in the gaseous medium is to be measured;

a second metal component located within the housing;

a gaseous medium passage located between an outside surface of the second metal component and an inside surface of the housing to permit passage of the gaseous medium to the electrochemical cell via the membrane and the orifice;

a third metal component located inside the recess and over the second metal component, the third metal component exerting a pressure on the second metal component and, via the second metal component, on an entire area located within a lower surface area of the second metal component the membrane; and at least one vertical orifice located within the third metal component, the at least one vertical orifice in communication with the gaseous medium passage to provide a feed passage for the gaseous medium to be analyzed from an exterior of the sensor to the electrochemical cell.

7. The sensor of claim 6, wherein the outer polymer envelope is welded to the upper part of the casing.

8. The sensor of claim 6, wherein the gas is oxygen.

9. The sensor of claim 6, wherein the gaseous medium passage is approximately 0.05 mm.

10. The sensor of claim 6, wherein the membrane forms a Knudsen-type diffusion barrier.

11. The sensor of claim 6, wherein the membrane completely covers the bottom of the housing.

12. The sensor of claim 6, wherein, a lateral wall of the recess comprises a first thread;

a lateral wall of the third metal component comprises a second thread, and the third metal component is screw threaded into the recess by the second thread engaging the first thread.

13. The sensor of claim 12, wherein the second and third metal components are arranged to avoid applying a shearing load to an upper surface of the membrane.

14. The sensor of claim 13, wherein the second metal component remains rotation free during the third metal component being screw threaded into the recess while the third metal component exerts pressure on the second metal component.

15. The sensor of claim 6, wherein, the first metal component is made from a corrosion-insensitive material.

16. The sensor of claim 6, wherein at least one of the first, second, and third metal comprises a plastic material.

17. The sensor of claim 6, wherein each of second and third metal components include contact surfaces exhibiting a roughness Ra of more than 0.8.

18. A sensor for measuring the partial pressure of a gas in a gaseous medium, comprising:

a cylindrical casing;

an electrochemical cell enclosed within the casing, the electrochemical cell comprising an anode, a cathode, and an electrolyte;

a cap plugging an upper part of the casing, the cap comprising an outer polymer envelope leaktightly joined to the upper part of the casing, a first component jacketed laterally by the polymer envelope, the first component having a central recess and an orifice in a bottom of the recess, the orifice opening out onto an upper part of the electrochemical cell;

a housing substantially centered in the bottom of the recess;

a porous membrane located at a bottom of the housing and over the orifice, the membrane forming a diffusion barrier for the gas whose partial pressure in the gaseous medium is to be measured;

a second component located within the housing;

a gaseous medium passage located between an outside surface of the second component and an inside surface of the housing to permit passage of the gaseous medium to the electrochemical cell via the membrane and the orifice;

a third component located inside the recess and over the second component, the third component exerting a pressure on the second component and, via the second component, on an entire surface area of the membrane located below the second component; and at least one vertical orifice located within the third component, the at least one vertical orifice in communication with the gaseous medium passage to provide a feed passage for the gaseous medium to be analyzed from an exterior of the sensor to the electrochemical cell.

19. The sensor of claim 18, wherein an interface between the second component and the third component is of low friction such that a rotational movement of the third component is not transferred to the second component.

* * * * *